US011903778B2

(12) United States Patent
Hoegerle et al.

(10) Patent No.: US 11,903,778 B2
(45) Date of Patent: Feb. 20, 2024

(54) INTEGRATED RFID TAG HOLDER

(71) Applicant: Aesculap AG, Tuttlingen (DE)

(72) Inventors: Roland-Alois Hoegerle, Tuttlingen (DE); Frederick Lenzenhuber, Tuttlingen (DE); Ralf Pfister, Trossingen (DE)

(73) Assignee: Aesculap AG, Tuttlingen (DE)

( * ) Notice: Subject to any disclaimer, the term of this patent is extended or adjusted under 35 U.S.C. 154(b) by 33 days.

(21) Appl. No.: 17/635,052

(22) PCT Filed: Aug. 19, 2020

(86) PCT No.: PCT/EP2020/073206
§ 371 (c)(1),
(2) Date: Feb. 14, 2022

(87) PCT Pub. No.: WO2021/032782
PCT Pub. Date: Feb. 25, 2021

(65) Prior Publication Data
US 2022/0287797 A1    Sep. 15, 2022

(30) Foreign Application Priority Data
Aug. 20, 2019 (DE) .................... 10 2019 122 349.0

(51) Int. Cl.
*A61B 90/98* (2016.01)
*G06K 19/07* (2006.01)

(52) U.S. Cl.
CPC .......... *A61B 90/98* (2016.02); *G06K 19/0723* (2013.01)

(58) Field of Classification Search
CPC ............................ A61B 90/98; G06K 19/0723
(Continued)

(56) References Cited

U.S. PATENT DOCUMENTS 8,830,033 B1 *   9/2014   Duxbury ........... H04M 1/72457
                                                 340/7.61
9,033,251 B2     5/2015   Weisshaupt et al.
(Continued)

FOREIGN PATENT DOCUMENTS

DE    102016121478 A1    5/2018
EP         1308883 A1    5/2003
(Continued)

OTHER PUBLICATIONS

Written Opinion received in International Application No. PCT/EP2020/073206 dated Nov. 18, 2020, with translation, 15 pages.
(Continued)

*Primary Examiner* — Michael G Lee
*Assistant Examiner* — David Tardif
(74) *Attorney, Agent, or Firm* — Christopher A. Rothe; Culhane Meadows PLLC

(57) ABSTRACT

A medical instrument, medical treatment system and method of assembly. The medical instrument has an instrument body with an RFID tag. An underfloor tag holder receives the RFID tag to fix it in position in such a way that the RFID tag is exposed to the surroundings of the instrument via an opening formed in an instrument body surface, but is set back from the instrument body surface to preferably prevent protrusion beyond the instrument body surface. At least portions of the underfloor tag holder with the RFID tag are enclosed by a separate metal shield having a signal-permeable aperture opening.

20 Claims, 7 Drawing Sheets

(58) Field of Classification Search
USPC .......................................................... 235/492
See application file for complete search history.

(56) References Cited

U.S. PATENT DOCUMENTS

| | | | | |
|---|---|---|---|---|
| 2007/0262867 | A1* | 11/2007 | Westrick | G06K 19/07771 |
| | | | | 340/572.7 |
| 2013/0186243 | A1 | 7/2013 | Harper et al. | |
| 2016/0196456 | A1* | 7/2016 | Mortensen | G16H 40/20 |
| | | | | 340/10.1 |
| 2019/0298484 | A1* | 10/2019 | Aquino | A61B 90/98 |
| 2019/0304598 | A1* | 10/2019 | Hansen | A61F 15/00 |

FOREIGN PATENT DOCUMENTS

| | | | | |
|---|---|---|---|---|
| EP | 1846873 | A2 * | 10/2007 | ............. A61B 34/20 |
| EP | 2929853 | A2 | 10/2015 | |
| EP | 3193284 | A1 | 7/2017 | |
| EP | 3395291 | A1 | 10/2018 | |
| FR | 2957240 | A1 | 9/2011 | |
| WO | 2006067610 | A2 | 6/2006 | |
| WO | 2015177538 | A1 | 11/2015 | |

OTHER PUBLICATIONS

Search Report received in German Application No. 10 2019 122 349.0 dated May 18, 2020, with translation, 21 pages.
Search Report received in International Application No. PCT/EP2020/073206 dated Nov. 18, 2020, with translation, 6 pages.

* cited by examiner

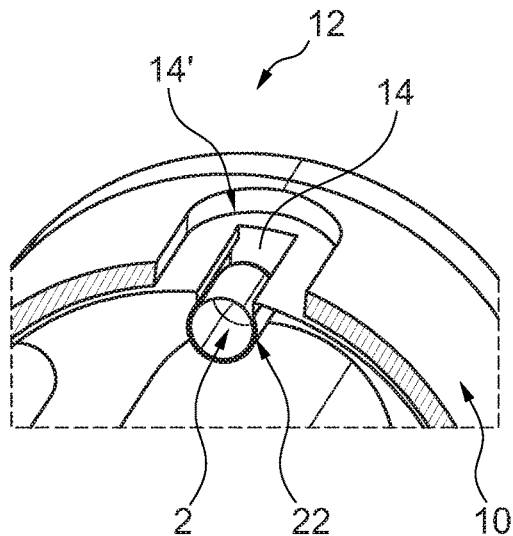
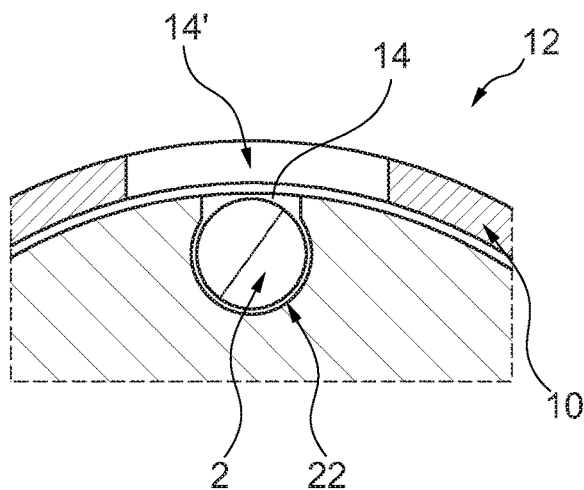
Fig. 14  Fig. 15
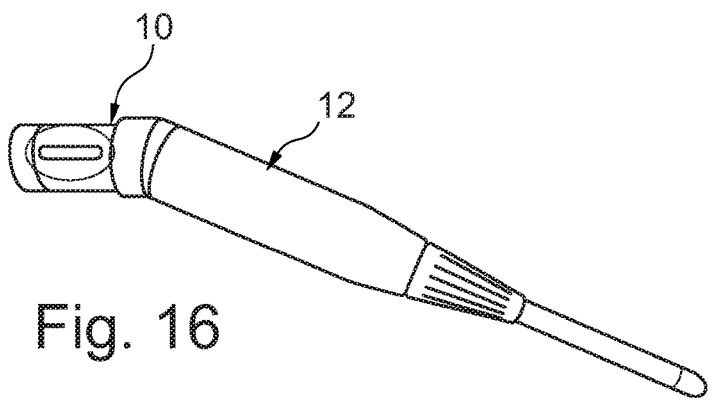
Fig. 16
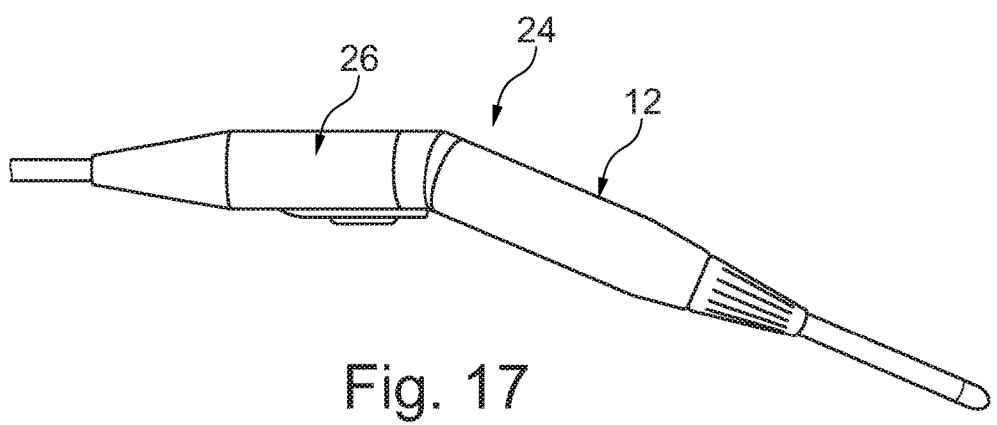
Fig. 17

INTEGRATED RFID TAG HOLDER

CROSS-REFERENCES TO RELATED APPLICATIONS

This application is the United States national phase entry of International Application No. PCT/EP2020/073206, filed Aug. 19, 2020, and claims priority to German Application No. 10 2019 122 349.0, filed Aug. 20, 2019. The contents of International Application No. PCT/EP2020/073206 and German Application No. 10 2019 122 349.0 are incorporated by reference herein in their entireties.

FIELD

The invention relates to a medical device for equipping a medical instrument with an RFID tag, comprising a holder or RFID tag carrier which is provided and adapted to receive an RFID tag. In addition, the invention relates to a medical treatment system and a method of assembly.

BACKGROUND

Medical (marking) devices with RFID tags are already known. For example, EP 3 193 284 A1 discloses an RFID marking element for equipping surgical instruments, which can be subsequently applied to the surface side of such a surgical instrument. The RFID marking element consists of a metal frame with a non-conductive cover, in the interior space of which an RFID chip is inserted. Furthermore, one side of the metal frame is attached to the surgical element, for example by welding.

WO 2015/177 538 A1 also discloses an RFID tag assembly in which a radio frequency transmissive cover is attached to a metal frame, wherein an RFID chip is accommodated in the hollow space that these two components jointly form. Here, the metal frame is subsequently attached to the surface side of a surgical element.

Although such RFID tags are comparatively small components, the RFID tag assemblies/devices subsequently applied in the prior art, however, form additional attack surfaces for contaminants and are also a hindrance when handling the surgical elements. Additionally applied RFID tags may form gaps and crevices in which germs or the like may be deposited, which is obviously very disadvantageous in medicine. In addition, the subsequently applied RFID tags may restrict the handling of the ergonomically-shaped surgical instruments and, in the worst case, may form corners and edges where a surgeon's glove may be damaged on contact or may receive a hole or tear.

In principle, of course, it is possible to place an RFID tag or, respectively, a corresponding (marking) device at such a position on the corresponding medical instrument where the least possible negative influence on instrument handling can be expected. However, this massively restricts the variety of positioning options depending on the type of instrument and may have to accept a decline, for example, in data transmission capability and the like.

A further disadvantage in the prior art is that passive RFID tags have to be placed at a short distance from a readout device due to their sometimes short transmission range. For this reason, in the prior art it is often only possible to apply the RFID tags subsequently to an outer surface of a surgical instrument in order to keep the distance between the RFID chip and the readout device as short as possible. For the above-mentioned reasons, care must be taken to ensure that the outer surface provided for this purpose is located at an instrument site that has only a minor influence on instrument handling and still permits sufficient readout quality.

It has therefore become apparent that not all medical instruments are suitable for subsequent equipping with an RFID tag according to the current procedure.

SUMMARY

Thus, the object of the present invention is to provide a medical device or, respectively, a medical/surgical instrument (of any type) with an RFID tag, a medical treatment system as well as a method for mounting/assembling, which ensures proper and safe handling both with regard to the instrument properties as such as well as to the data transmission properties of the RFID tag. Preferably, a further object of the present invention is to ensure good cleaning and/or sterilization of the device according to the invention/ of the medical instrument equipped therewith. An additional object of the invention is further preferably to ensure reception enhancement of inserted/applied RFID tags.

The core of the present invention essentially consists in forming or providing the medical instrument to be equipped at an individually selected surface location (particularly suitable for interference-free data transfer) with a holder either in the form of an (instrument-integral) receiving pocket or recess, preferably in groove/slit form, or in the form of a preferably slit-shaped cutout in a hollow space of the instrument located thereunder, wherein a tag carrier/ holder having the receiving pocket or recess preferably in groove/slit form is inserted into this hollow space.

The depth of the receiving pocket with respect to the corresponding instrument surface as well as its (width-height) dimensions are preferably selected such that a (single) RFID tag can be inserted/placed into the receiving pocket in the manner of a battery receptacle compartment, wherein the RFID tag terminates (flush) at its jacket side at maximum on the plane of the corresponding instrument surface or even remains recessed with respect to this plane, i.e. it is recessed in the receiving pocket (so-called underfloor arrangement). In this way, the surface structure of the instrument (in the absence of protrusion/projection of the RFID tag above the instrument surface) remains essentially unaffected and the data transfer property is nevertheless (maximally) preserved.

In the preferred embodiment, the medical device thus comprises a holder integrated or (additionally) insertable into the body of the medical instrument, which is or forms the aforementioned receiving pocket opening at the/a surface of the medical instrument, which is provided and adapted to receive at least one (single) RFID tag.

In other words, the medical device has the holder for at least one RFID tag integrated into the medical instrument or (additionally) inserted within the medical instrument. This means that the holder according to the invention does not affect the normal (outer) shape of the medical instrument by a subsequently attached RFID tag, but that the holder of the RFID tag is integrated or arranged below the/an outer surface of the medical instrument. In yet other words, the holder is integrated/built in/formed/shaped (hereinafter only referred to as 'integrated') into the housing/the shape/the structure/the body of the medical instrument (hereinafter only referred to as 'body') or is respectively integrated/ inserted within the body of the medical instrument. The holder may be integrated in the body of the medical instrument itself in one piece of material/as a single component together with the medical instrument, namely as a recess/ cavity/groove/milling/hollow space/pocket (hereinafter only referred to as receiving pocket) (wherein in this case the receiving pocket formed in the instrument body as well as a (tag insertion) opening formed on the surface of the instrument body are substantially adapted to the tag shape), or the holder may be integrated/inserted as an individual/separate component (tag carrier) in the body of the medical instrument (e.g. in a hollow space in the medical instrument) (wherein in this case the shape of the (signal passage) opening formed on the surface of the instrument body may be essentially universal, since the separate holder is already equipped with the tag and the holder has been inserted into the hollow space of the medical instrument (possibly via a separate access)).

In other words, the medical instrument or, respectively, the instrument body or a part of the instrument itself may be provided with a tag-receiving pocket as holder, or a separate tag carrier with a receiving pocket formed therein may be provided as holder, which is/will be inserted into a (possibly already existing) hollow space in the medical instrument, wherein the medical instrument in this case has an opening/cut-out to this hollow space, in the area of which the RFID tag comes to rest when the holder is inserted.

The underfloor tag holder with the RFID tag is surrounded, at least in sections, in particular by a separate metal shield with a signal-permeable aperture opening, wherein the aperture opening forms the opening, in particular the radially outer opening, towards the surroundings of the instrument. This improves the data transmission quality and increases the possible transmission distance.

The RFID tag is preferably always installed in an underfloor manner (i.e. set back with respect to the instrument surface) so that the RFID tag is placed underneath the opening and not protruding above it.

Preferably, the medical instrument is a surgical instrument, a monopolar HF instrument, a bipolar HF instrument, an ultrasound instrument, an electrosurgical or purely mechanical instrument, a surgical clamp, surgical forceps, a container, surgical scissors, a scalpel, and/or the like. Particularly preferably, the medical instrument is a handpiece with an integrated motor and/or a tool that is couplable by engagement to the handpiece.

Furthermore preferably, the RFID tag is an RFID transponder for storing information associated with a specific object (in this case the medical instrument). This so-called 'identifier' can be individualized according to the requirements of the respective process. Preferably, the RFID tag consists of:
- at least one microchip, preferably in the size of a few millimeters in diameter,
- at least one antenna, preferably in the form of a coil,
- at least one carrier or housing, wherein the housing is preferably waterproof and/or airtight and preferably protects the transponder electronics from the environment,
- in the case of an active RFID tag, additionally at least one energy source, preferably a battery/accumulator or a capacitor.

In the case of passive transponders, the energy supply is provided externally via the antenna. Preferably, the RFID tag of the invention is a passive RFID tag. Preferably, the RFID tag further comprises a (rod-shaped) ferrite core with a coil wound around it. Preferably, the RFID tag may be in the form of an NFC tag or, respectively, NFC chip (Near Field Communication).

The RFID tag is provided for and adapted to store at least one of the following information, in particular encrypted, or respectively is characterized by the following storage data:

general condition
lifetime/end of life
maintenance interval
performance and suitability for subsequent operation
product maintenance shortfall and product damage, if applicable
temperature overshoot and undershoot and product damage, if applicable
item number
serial number
customer number Preferably, in the present medical device, at least one RFID tag is inserted in the holder or, respectively, in the receiving pocket, further preferably the RFID tag has a cylindrical shape with rounded ends. In other words, in the medical device preferably the RFID tag is already contained/installed/inserted. The shape of the RFID tag is further preferably in pill form.

Further preferably, the receiving pocket in the medical instrument or in the tag carrier has the shape of an elongated slit or a groove adapted to receive the preferably cylindrical/pill-shaped RFID tag 'lying', i.e. in the manner of a (flat) battery compartment.

Preferably, the RFID tag has an outer surface/a housing made of a material that is permeable to radio frequencies and is further preferably waterproof and/or airtight. In other words, the housing of the RFID tag is made of a radio-frequency permeable/signal-permeable material such as glass, ceramic, plastic, thermoplastic, material marketed under the trademark DUROPLAST™, plastics in general and/or silicone, particularly preferably of a non-metallic material, with which the ferrite core together with the coil and chip wrapped around it are encapsulated.

In principle, the geometry and the material of the medical instrument and of the RFID tag, or respectively its body, as well as the orientation of the receiving pocket with respect to the corresponding instrument surface are freely selectable. Preferably, however, a receiving pocket is parallel to the RFID tag, in particular the coil of the RFID tag, in such a way that the RFID tag is oriented in its longitudinal direction parallel to the outer surface of the body of the medical instrument (i.e. 'lying'). The receiving pocket may optionally remain free/open to the outside or may be filled/closed with a signal-permeable material. In other words, the receiving pocket or, respectively, the opening to the receiving pocket formed in the medical instrument may be provided with or without a cover made of the signal-permeable material. Finally, the RFID tag may already be formed per se in the manner of a sealing cap in such a way that, when the RFID tag is inserted into the receiving pocket, this pocket or respectively its opening is sealed to the outside (water-tight/air-tight) by the RFID tag itself.

The RFID tag or the cover may be flat/level/terminating/flush with the (outer) surface of the medical instrument. The cover, as explained above, is preferably made of a material that is permeable to radio frequencies and further preferably seals the receiving pocket/holder watertight and/or airtight to/with the outer surface of the medical instrument. Moreover, in the case of a separate tag carrier, the opening/cut-out in the instrument connecting the hollow space of the instrument to the outside and the possibly associated cover may, of course, have any geometric shape, since the additional separate holder/tag carrier is inserted quasi as an adapter in the hollow space of the instrument, wherein the receiving pocket adapted to the RFID tag is formed in the tag carrier (i.e. no receiving pocket is formed in the medical instrument itself). In this case, the opening no longer serves to insert the RFID tag into the receiving pocket (as is inevitably the case with an instrument-integral receiving pocket) but merely as an input/output (passage) for the radio frequency signals.

If a signal-permeable core and/or socket is chosen as the tag carrier/holder of the RFID tag (e.g. thermoplastic, material marketed under the trademark DUROPLAST™, plastics in general, silicone, etc.), the reading and writing distance is optimized by a metal shield/reflector at least partially surrounding the carrier, which distances the RFID tag from a reading/readout/writing device (hereinafter only referred to as reading device), with a geometrically defined opening in the area of the receiving pocket in the separate tag carrier. In other words, in one embodiment, the holder/tag carrier may be formed as a signal-permeable core (e.g., plastic) that is located in a medical instrument or that is/will be inserted into a hollow space of the instrument. The holder (receiving pocket in the tag carrier) is provided and adapted to receive at least one RFID tag.

Further preferably, the opening of the holder, i.e. the opening of the receiving pocket integrally formed in the instrument body or the opening/slit/cut-out formed in the instrument in case of a separate holder/tag carrier serving as a passage for radio signals, has a (slit) width corresponding to the product of the coil diameter and an ideal factor, wherein the ideal factor is in the range of 1.3 to 2.2, more preferably in the range of 1.6 to 1.9 and is particularly preferably 1.75. In other words, the opening on the medical instrument that is parallel to the RFID tag has a width that is greater than the coil diameter of the RFID tag and/or of the RFID tag itself.

Further preferably, the opening of the holder in the case of an instrument body-integral receiving pocket or the opening/slit/cut-out formed in the instrument in the case of a separate holder/tag carrier serving as a passage for radio signals has a length that is −30% up to +50% of the total length of the ferrite core, further preferably a length of 0% up to +30% of the total length of the ferrite core and particularly preferably a length of +15% of the total length of the ferrite core. In other words, the opening on the medical instrument that is parallel to the RFID tag has a length that is preferably greater than the length of the ferrite core and/or of the RFID tag.

In addition, the RFID tag preferably uses a frequency band in the range of 12 to 15 MHz, advantageously in the range of 13 to 14 MHz, further preferably in the range of 13.4 to 13.7 MHz and particularly preferably of 13.56 MHz.

Further preferably, the invention relates to a system consisting of a medical device with the above features and a readout device that is couplable to the medical device. In other words, the medical device may be readout by a readout device that can be brought into close proximity, i.e. a distance smaller than one centimeter, to the RFID tag. In the case of medical devices that have a connection, for example for an air supply/power supply and/or data exchange, this readout device may be attached to the medical device in the couplable plug/socket for the counterpart.

Furthermore, the invention relates to a method for mounting/assembling a medical instrument according to the invention. First, the step of positioning the RFID tag, the medical instrument and the metal shield relative to each other is performed. In particular, a terminal coupling portion of the medical instrument or, respectively, the instrument body has a longitudinal axis/axial axis, in the extension of which the metal shield is positioned, preferably coaxially. After this, the RFID tag is placed in the underfloor tag holder of the medical instrument provided for it, in particular placing it in the radial direction, preferably pressing it into the underfloor tag holder in the radial direction. Furthermore, the step of rotating the metal shield around the longitudinal axis/axial axis of the medical instrument may preferably be performed until the signal-permeable aperture opening and the RFID tag are in the same position in the circumferential direction. Viewed in the direction of the longitudinal axis, the aperture opening and the RFID tag are then at the same angle to each other in the circumferential direction or, respectively, in the radial extension. Finally, the metal shield is slid onto the medical instrument in the axial direction (in the direction of the longitudinal axis of the portion of the instrument body that receives the RFID tag), so that the aperture opening and the RFID tag are arranged in radial extension and, in particular, in the same axial position relative to each other, and the RFID tag is fixed in position in the medical instrument by the metal shield so that it cannot be lost. Preferably, the method may comprise the step of fixing the metal shield to the medical instrument or, respectively, to the instrument body.

According to a preferred embodiment, the method, in particular prior to the step of sliding on, may further comprise the steps of: positioning a signal-permeable cover relative to the metal shield; placing/inserting the cover in the signal-permeable aperture opening by sliding the cover radially inwards in the axial direction into the metal shield and sliding the cover outwards in the radial direction into the aperture opening, so that the cover is inserted into the aperture opening and after the step of sliding on the metal shield, the cover is fixed in position in the medical instrument so that it cannot be lost. Due to a coordinated geometry of the cover with the undercut to the aperture opening, the cover cannot be displaced outwards in the radial direction or perpendicularly to the longitudinal axis and is held securely against loss, since after the step of sliding on, the RFID tag rests radially on the inside and in the axial direction the cover abuts the edges of the aperture opening.

BRIEF DESCRIPTION OF THE DRAWING FIGURES

The invention is explained in more detail below based on preferred configuration examples and with reference the accompanying figures.

FIG. 14 is another perspective representation illustrating an example of a medical instrument with an RFID tag integrated into the body of the medical instrument;

FIG. 15 is a side view of the medical instrument of FIG. 14;

FIG. 16 is a representation illustrating an example of a system consisting of a medical instrument and a coupling that is couplable thereto shown in a disconnected state;

FIG. 17 is a representation illustrating an example of a system consisting of a medical instrument and a coupling couplable thereto shown in a connected state;

FIGS. 27 to 31 each show perspective partial views of a medical instrument according to another preferred embodiment, wherein a step-by-step assembly of said medical instrument according to a method for mounting a preferred embodiment is shown.

DETAILED DESCRIPTION

Configuration examples of the present disclosure are described below based on the accompanying figures.

Figure 1:
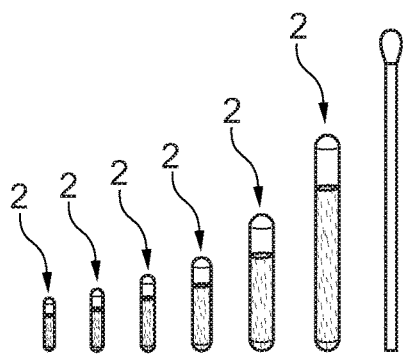
FIG. 1 is a representation illustrating RFID tags that are usable according to the invention.
Figure 2:
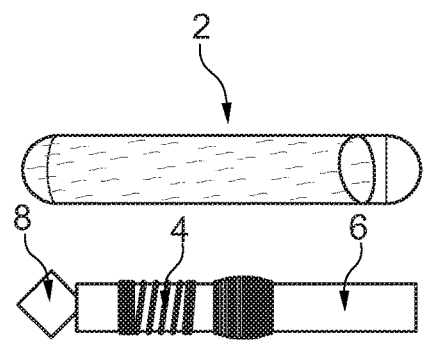
FIG. 2 is another representation illustrating RFID tags that are usable according to the invention.

FIG. 1 is a representation illustrating RFID tags 2 usable according to the invention. Here, the various sizes of RFID tags 2, in particular so-called glass RFID tags, are shown next to a commercially available matchstick. Accordingly, the RFID tags 2 have a cylindrical shape with rounded ends, resembling a rod or pill shape. Such RFID tags essentially belong to the prior art and therefore do not require any further description. Nevertheless, FIG. 2 shows another representation at least for basic illustration of an RFID tag 2 usable according to the invention in a closed/encapsulated state (FIG. 2, top) and the components located in a (glass) housing of the RFID tag (FIG. 2, bottom). Accordingly, a coil 4 is provided, which is wound centrally around a rod-shaped ferrite core 6 and is in contact with an RFID chip 8. The RFID chip 8 is here placed at an axial end of the ferrite core 6. This construction consisting of the ferrite core 6, the coil 4 surrounding it in sections and the RFID chip 8 arranged axially at the end are enclosed by a radio wave permeable material, e.g. a glass material, which forms the housing of the RFID tag 2.

Figure 3:
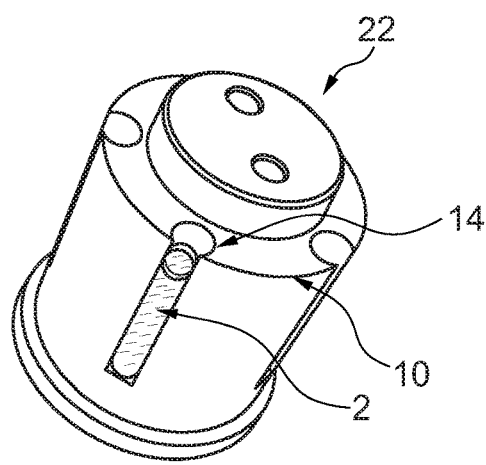
FIG. 3 is a representation illustrating an example of a holder/tag carrier with an RFID tag to be integrated into the body of a medical instrument.

FIG. 3 is a representation for illustrating a first example of a holder/tag carrier 22 according to the invention for a medical instrument not further shown in FIG. 3. The holder/tag carrier is formed as a separate component and provided for insertion into an (already existing) hollow space in the medical instrument and is adapted, if applicable, wherein the separate holder/tag carrier 22 is formed with a (single) slit-shaped/groove-shaped receiving pocket 14 for the RFID tag 2. The cartridge-shaped, separate holder/tag carrier 22 in the present example consists in this case of a (cylindrical) metal block, in the lateral surface of which the elongated groove/receiving pocket 14 is introduced parallel to the longitudinal axis of the metal block, into which the RFID tag 2 is axially inserted/slid. The elongated receiving pocket/groove 14 is provided and adapted for receiving the RFID tag 2 and therefore has a shape that corresponds to the shape of the RFID tag 2. The receiving pocket 14 is designed in such a way that it breaks through the outer surface of the metal block and thus forms an elongated slit. The slit or, respectively, the groove opening is narrower than the receiving pocket 14 itself, so that the RFID tag 2 inserted into the receiving pocket 14 cannot fall out of the slit-shaped opening or, respectively, cannot be pressed out. Accordingly, at least one axial end of the elongated receiving pocket/groove 14 is open at a front side of the metal block so that the RFID tag 2 can be axially inserted into the receiving pocket/groove 14. Thus, the RFID tag 2 is visible from the outside along the jacket-side outer surface of the metal block through the slit/groove opening.

Figure 4:
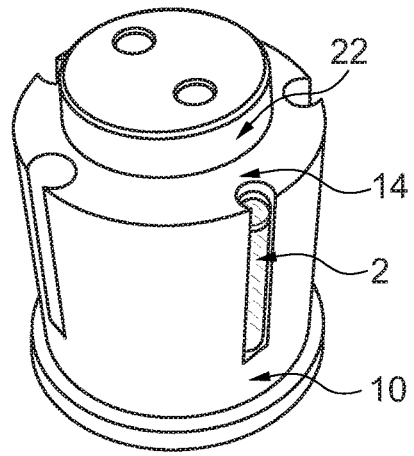
FIG. 4 is another representation illustrating an example of a holder/tag carrier with an RFID tag to be integrated into the body of a medical instrument.

FIG. 4 is a further representation illustrating a second example of a separate tag carrier 22 insertable into the body or, respectively, into the hollow space of a medical instrument formed thereby (not shown in FIG. 4), wherein the tag carrier 22 is also formed with a groove-shaped receiving pocket 14 for the RFID tag 2 according to the previously described configuration example. However, in contrast to the previous configuration example, the tag carrier 22 in this case consists of a non-metallic, or respectively signal-permeable, preferably plastic block, into which the elongated, groove-shaped receiving pocket 14 is inserted parallel to the longitudinal axis of the plastic block, into which the RFID tag 2 is axially inserted. Thus, the embodiment (construction) according to FIG. 4 is analogous to FIG. 3 with the difference of the material of the tag carrier 22. Due to the fact that the material of the tag carrier 22 is signal-permeable, a better reception of the RFID tag 2 is achieved.

Figure 5:
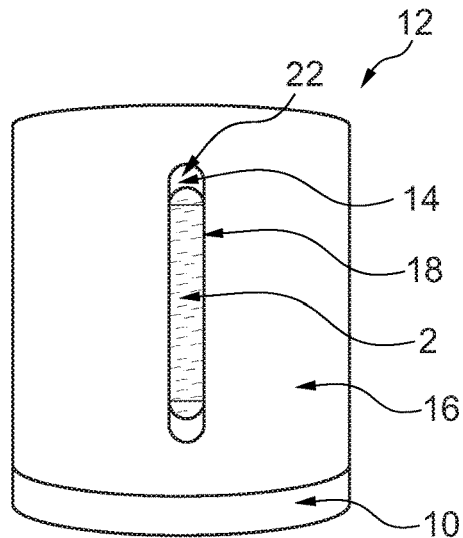
FIG. 5 is a representation illustrating an example of a medical instrument with an RFID tag integrated into the body of the medical instrument and an outer housing.

FIG. 5 is a further representation illustrating an example of a medical instrument 12 or, respectively, of the medical device with a separate tag carrier 22 insertable into the body 10 (or, respectively, its hollow space) of the medical instrument (not further shown in FIGS. 5 and 6), wherein the tag carrier 22 is formed with the groove-shaped receiving pocket 14 for the RFID tag 2 according to the second configuration example described above. In this case, the tag carrier 22 consists of the cylindrical, non-metallic, preferably plastic block comparable to the immediately previously described second configuration example according to FIG. 4, but with an additional outer housing or outer sleeve 16 made of a metallic material. The outer housing 16 has a slit-shaped outer housing opening 18, which is parallel or respectively overlapping/covering the receiving pocket 14 in the plastic block and thus runs parallel to the RFID tag 2 arranged in the receiving pocket 14. In this third example, however, the length of the outer housing opening 18 is longer than the RFID tag 2, and the width of the outer housing opening 18 corresponds (exactly) to the width of the slit-shaped opening of the receiving pocket 14. The width of the slit-shaped opening of the receiving pocket 14 and thus of the outer housing opening 18 is therefore smaller than the diameter of the RFID tag 2 in order to prevent the RFID tag 2 from falling out of the tag carrier (separate holder) 22 or, respectively, of the receiving pocket 14 formed therein, as already described above. However, due to the increased length of the outer housing opening 18 compared to the receiving pocket 14, an improved reception is achieved compared to the first configuration example according to FIG. 3. The metallic outer sleeve 16 also serves as a reflector or metal shield to further improve the transmitting/receiving properties (directivity) of the RFID tag 2 in the direction of the readout device (not shown in FIGS. 5 and 6).

Figure 6:
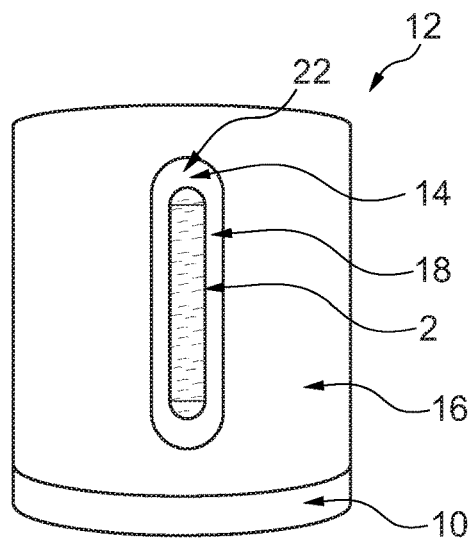
FIG. 6 is another representation illustrating an example of a medical instrument with an RFID tag integrated into the body of the medical instrument and an outer housing.

FIG. 6 is another representation illustrating an example of a medical instrument 12 or, respectively, of the medical device according to the invention with the separate tag carrier 22 insertable into the body 10 or, respectively, a hollow space of the medical instrument, and formed with the groove-shaped receiving pocket 14 for the RFID tag 2 according to the third configuration example described immediately above and consequently provided with a metallic outer sleeve or outer housing 16. The structure is therefore analogous to the third embodiment according to FIG. 5 with the exception that the width of the slit-shaped outer housing opening 18 according to FIG. 6 is larger than the width of the opening of the receiving pocket 14 in the plastic block and/or even of the RFID tag 2 itself. Since the material of the tag carrier 22 is signal-permeable (e.g. a plastic material) and the outer housing opening 18 is wider than the slit width in the tag carrier 22, an even better reception of the RFID tag 2 is achieved and a directivity is still maintained by the metal outer sleeve 16 acting as a reflector.

Figures 7, 8:
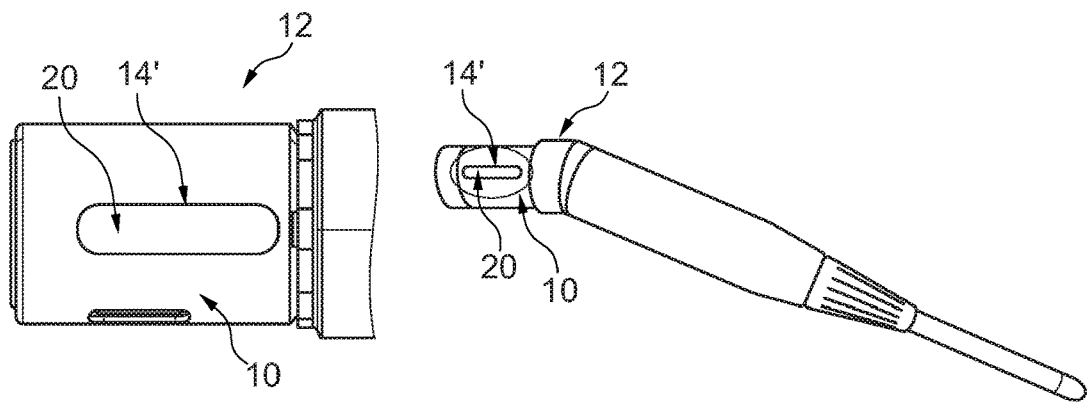
FIG. 7 is a representation illustrating an example of a medical instrument with an RFID tag integrated into the body of the medical instrument and a cover.
FIG. 8 is a representation illustrating an example of a medical instrument with an RFID tag integrated into the body of the medical instrument and a cover.

FIG. 7 is a representation illustrating another example of a medical instrument 10 with a hollow space, in this case a (motor-equipped/equippable) handpiece, with an RFID tag (not shown) integrated in the body 10 of the medical instrument/handpiece and an (optional) cover 20 over the RFID tag. The cover 20 is preferably inserted flat with the outer surface of the body 10 into the opening 14', which is formed on an outer surface of the medical instrument/handpiece or respectively of its body 10.

Such a handpiece is sufficiently known from the prior art and therefore requires no detailed description. In principle, however, the handpiece according to FIG. 7 has a preferably cylindrical/sleeve-shaped gripping portion, at the distal end of which a tool coupling is arranged and at the proximal end of which a motor coupling is arranged. In these always identically designed connection/coupling portions of the handpiece and in particular in the proximal coupling area for the motor, the RFID tag can be integrated or respectively inserted. Preferably, the separate RFID tag carrier 22 according to one of the first to fourth configuration examples is used for this purpose, which, however, is further preferably a plastic core with surrounding metal shielding according to the above description. As already explained, the plastic core incorporates the groove-shaped receiving pocket 14 into which the RFID tag is inserted and which has a slit-shaped opening.

The handpiece is also formed in its proximal coupling portion with a longitudinal slit 14', which connects the hollow space of the instrument formed by the proximal coupling portion with the surroundings and which overlaps with the slit-shaped opening in the RFID tab carrier already inserted in the hollow space (see FIGS. 3-6) and thus exposes the RFID tag to the outside. The longitudinal slit 14' formed in the handpiece or, respectively, in its proximal coupling portion and optionally the receiving pocket 14 located thereunder in the inserted tag carrier 10 is preferably closed by a plastic part/cover 20 in such a way that a substantially smooth/plane surface results on the outside of the handpiece in the area of the longitudinal slit 14'.

FIG. 8 is another representation for the entire illustration of the medical instrument 12 of FIG. 7, more specifically of the handpiece according to FIG. 7 with a connectable motor not shown in FIG. 8, wherein from FIG. 8 the placement of the RFID tag on/in the handpiece is more clearly visible. Accordingly, the RFID tag is arranged in the handpiece or, respectively, in its hollow space in such a way that it is located proximally to the handle portion of the handpiece, in particular in that axial portion of the handpiece or, respectively, of the body 10 which is inserted in a coupling manner into a motor housing, as described in more detail below.

Figures 9, 10, 11:
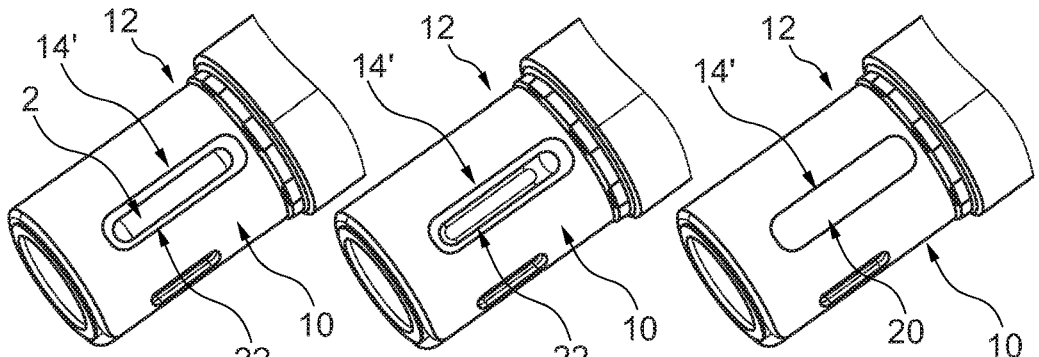
FIG. 9 is a representation illustrating an example of a medical instrument with a holder integrated into the body of the medical instrument.
FIG. 10 is a representation of the holder of FIG. 9 with an RFID tag integrated into the holder.
FIG. 11 is a representation of the RFID tag in the holder of FIG. 9 with a cover on the holder.

FIG. 9 is a representation illustrating a another example of a medical instrument 12 with a tag carrier/holder 22 integrated into the body 10 of the medical instrument. The tag carrier 22 is a separate component of its own, which is installed/inserted in the manner of an adapter in a preferably slit-shaped opening 14' of the body 10. In other words, the medical instrument 12 according to FIG. 9 corresponds to the one according to FIG. 8, wherein in this case a receiving pocket in the form of the aforementioned tag carrier/holder 22 is incorporated into the body of the medical instrument or respectively is inserted into the body's own slit, and wherein the inserted, separate receiving pocket is open at the outer surface of the instrument. The instrument-integral or respectively body-integral slit/opening 14' is not individually adapted to the tag to be placed therein (too large). For this reason, the additional tag carrier 22 is inserted into the slit/opening 14' as a receiving pocket, wherein the tag carrier 22 forms a receptacle substantially adapted to the tag.

The holder/tag carrier 22 is thus provided and adapted for receiving the RFID tag (not shown) in the manner of an adapter or intermediate piece between the (universally dimensioned) slit 14' in the instrument body and the (individually formed) receptacle in the holder/tag carrier 22. In the present case, the holder/tag carrier 22 is located below the outer surface of the body 10, i.e. it is set back with respect to the outer surface. The shape of the insertion/opening formed by the receptacle in the holder 22 corresponds to the shape of the RFID tag, which can simply be inserted into the insertion/opening of the holder/tag carrier 22 and can be held therein—possibly independently of the shape of the slit 14' formed in the instrument body.

FIG. 10 is a representation of the holder 22 in the body 10 of the medical instrument 12 of FIG. 9 with an RFID tag 2 integrated/inserted in the holder 22. As can be seen from this FIG. 10, the receptacle in the holder/tag carrier 22, which is formed as a separate component and inserted in the slit 14' in the instrument body 10, was dimensioned in such a way that the RFID tag remains behind the outer surface of the instrument body 10. This is necessary in this configuration example in that it leaves a receptacle area that can be filled with cover material, which on the one hand ensures a flat instrument surface, and on the other hand holds the RFID tag 2 in the receptacle.

FIG. 11 is a representation of this cover 20 on/in the holder 22 (not shown in FIG. 11) in the body 10 of the medical instrument 12 of FIG. 10 with the RFID tag integrated/inserted in the holder 22. The cover 22 is flat with the outer surface of the body 10.

Figure 12:
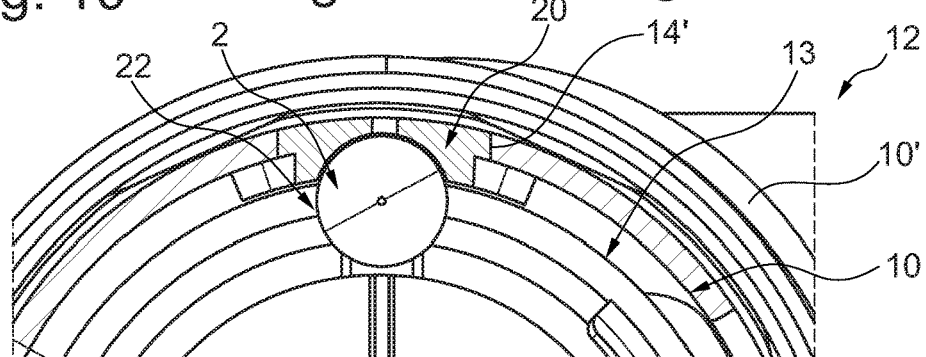
FIG. 12 is another representation illustrating an example of a medical instrument with an RFID tag integrated into the body of the medical instrument.

FIG. 12 is another representation illustrating an example of a medical instrument 12 with an RFID tag 2 integrated/inserted in the body 10 of the medical instrument. In this example, the holder 22 is in the form of a tag carrier according to one of the examples shown in FIGS. 3 to 6 and is inserted in a hollow space 13 of the instrument, in particular in the proximal coupling portion of the handpiece as shown in FIG. 8. Accordingly, a slit 14' connecting the hollow space 13 to the surroundings is formed in the instrument body 10. In addition, the housing or, respectively, the coupling portion 10' of a motor mounted on the coupling portion of the handpiece is indicated in FIG. 12.

A cover 20 is applied to the holder 22 or, respectively, is inserted in the slit 14'. The surface of the cover 20 is flush/plane with the outer surface of the body 10, so that the cover 20 together with the outer surface of the body 10 forms a plane/level or, respectively, gap-free/step-free surface. The holder 22 or, respectively, the tag carrier according to FIG. 12 also has elastic properties, which have the effect that a spring force is exerted on the RFID tag in the installed state of the holder 22 in the hollow space 13 of the instrument 12, which presses it radially outwards against the cover 20 and clamps it between itself and the cover 20.

Figure 13:
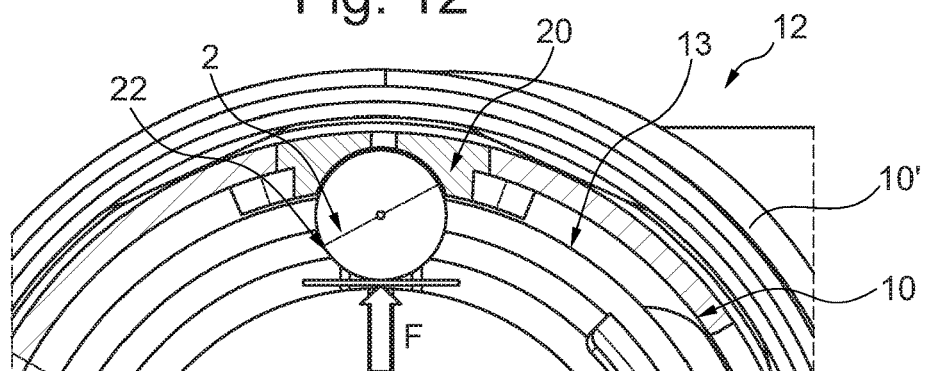
FIG. 13 is another representation illustrating an example of a medical instrument with an RFID tag integrated into the body of the medical instrument that is subjected to a spring force.

FIG. 13 is a representation to illustrate the example according to FIG. 12 with an RFID tag 2 which is inserted into the body 10 of the medical instrument 12 via of a (cartridge-like) holder 22 and which is subjected to the spring force mentioned above. The structure is analogous to the representation in FIG. 12, but the holder 22 is deformed by applying or respectively pressing the cover 20 into the slit 14' in such a way that a spring force F presses the RFID tag 2 against the cover in order to inhibit freedom of movement and thus to prevent mechanical damage. It should be explicitly noted that the spring force does not necessarily have to be generated by the elastic properties of the tag carrier 22, but that a separate spring, for example a gas cushion or the like, can also be arranged in the slit-shaped receiving pocket 14 in the tag carrier 22. It is also possible to manufacture the tag housing from an elastic material.

FIG. 14 is a further perspective, partially broken-up representation for illustrating an example of a medical instrument 12 with a (cartridge-shaped) tag carrier (holder) 22 inserted into the body 10 of the medical instrument or, respectively, into its hollow space according to one of the examples according to FIGS. 3 to 6, in whose receiving pocket 14 an RFID tag 2 is already inserted. In the outer surface of the body 10 there is a slit-shaped opening 14', which is located above the RFID tag 2 in the holder/tag carrier 22 and is larger in terms of its dimensions in width and length than the receiving pocket 14. Only the opening 14' in the instrument body 10 is provided in this embodiment and adapted to receive a cover (not shown). That is, the opening 14' together with the holder/tag carrier 22 inserted in the hollow space of the instrument forms an offset/step-shaped recess, such that it is possible to insert the RFID tag 2 via the opening 14' into the receiving pocket 14 in the inserted holder 22, as well as to insert the cover into the opening 14' in the instrument body 10 thereafter. In other words, the RFID tag 2 can also be inserted into the opening/receiving pocket 14 in the holder/tag carrier 22 after it has been inserted into the hollow space of the instrument, wherein the holder 22 of the RFID tag 2 or, respectively, the receiving pocket 14 formed therein ensures secure holding of the RFID tag 2 without the need for additional hold-down devices. The base material of the holder 22 or, respectively, of the tag carrier 22 in this case ideally consists of a signal-permeable material, as shown in FIG. 4. In this embodiment, the RFID tag 2 is in an underfloor placement with respect to the inner diameter of the body 10 forming the hollow space.

FIG. 15 is a cross-sectional view of the medical instrument 12 of FIG. 14 and serves to further illustrate the example of a medical instrument with an RFID tag 2 integrated into the body 10 of the medical instrument, or respectively inserted into the hollow space of the instrument, according to FIG. 14. As can be seen from this, the receiving pocket 14 formed in the tag carrier (holder) 22 forms a longitudinal groove with an opening slit that is slightly narrower than the inserted RFID tag 2, whereas the slit 14' in the instrument body 10 is significantly wider than the receiving pocket 14 and the RFID tag 2 located therein. This embodiment makes it possible to push the RFID tag 2 through the instrument slit 14' into the receiving pocket 14 (while slightly widening the pocket opening 14), wherein the RFID tag is subsequently held in the receiving pocket 14 by the opening cross-section.

FIGS. 16 and 17 are representations illustrating an example of a system 24 consisting of a medical instrument 12, as already shown in FIG. 8, and a motor 26 couplable thereto in separate (as shown in FIG. 16) and coupled (as shown in FIG. 17) states. Alternatively, instead of the couplable motor 26, a coupling connector or a coupling connecting element may be provided via which a driving force may be operatively coupled and introduced into the medical instrument accordingly. The motor 26 or respectively its coupling portion is provided and adapted to receive a part of the medical instrument, i.e. its proximal coupling portion according to FIGS. 7 to 11. The motor 26 has a readout device (not shown) in the area of its coupling portion, preferably on its inner side, which is positioned in such a way that, in a coupled state according to FIG. 17, the readout device and the RFID tag (not shown) are located in the immediate vicinity/in the radial direction opposite/parallel to each other. Alternatively, no readout device may be integrated in the motor 26, wherein in this case the RFID tag would only be readable in terms of time before the plugging process. During handling, the (motor) coupling 26 is pushed over the motor connector/body/part of the medical instrument and the RFID tag 2 is thus simultaneously mechanically protected as well as shielded against being read out.

Figure 18:
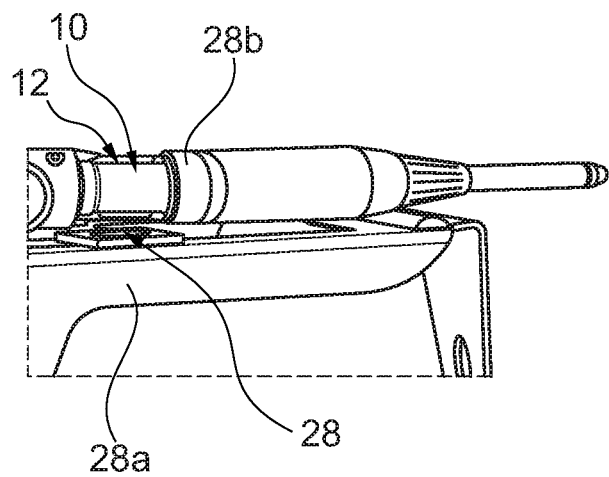
FIG. 18 is a representation illustrating an example of a system consisting of a medical instrument and a readout device.
Figure 19:
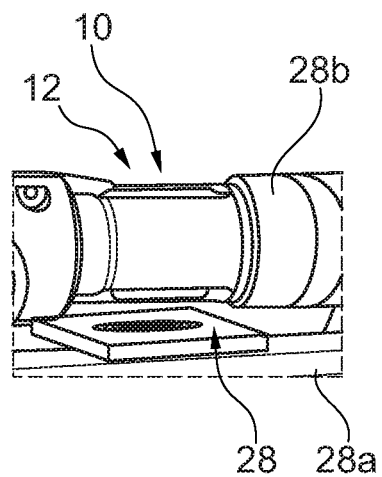
FIG. 19 is a detailed representation of FIG. 18.

FIGS. 18 and 19 each show a representation of an exemplary instrument system consisting of a medical instrument 12 with an instrument body 10 configured as an (electromotive) handpiece and a readout device 28 configured as an instrument holder. The position on the medical instrument at which the RFID tag is located is brought into the closest possible proximity to the readout device 28, whereby the RFID tag can be read out.

FIG. 19 is a detailed representation of the system of FIG. 18 consisting of the medical instrument and the readout device 28. Accordingly, the readout device 28 according to this preferred example has a rack or frame 28a to which at least one instrument receptacle is fixed, preferably in the form of a clamp or clip 28b, into which the medical instrument or, respectively, its instrument body 10 can be clamped (this clamping condition is shown enlarged in FIG. 19). Furthermore, in FIG. 19 the readout device 28 can be seen, which is located below the medical instrument when it is inserted into the instrument receptacle 28b. The decisive factor here is that the RFID tag, due to its arrangement according to the invention on the medical instrument, that is in an underfloor manner, can be positioned (as desired) in such a way that it comes to rest exactly above the readout device 28 when the instrument is inserted into the instrument receptacle 28b, thus minimizing the transmission distance between the RFID tag and the readout device 28.

Figure 20:
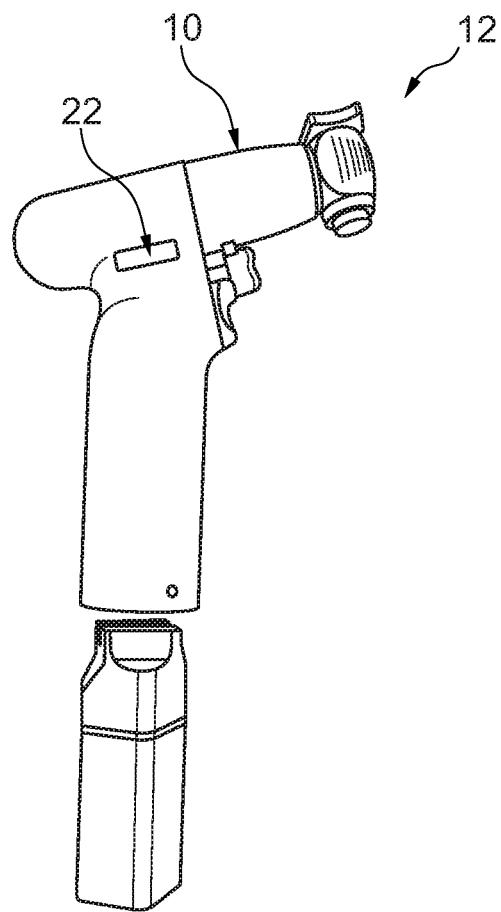
FIG. 20 is a representation illustrating an example of a medical instrument with an RFID tag holder.

FIG. 20 is a representation illustrating an example of a medical instrument 12 with RFID tag holder 22, wherein the medical device is a cordless drill. In this preferred example, the holder 22 is provided by a receptacle adapter embedded in an instrument slit, in which the RFID tag is inserted and covered by a filling material. The position of the RFID tag is not arbitrary, but selected so that the data can be read out as easily and precisely as possible using a readout device.

In particular, in this example, it is provided that the cordless drill is provided with a removable accumulator/battery which is insertable into a receptacle slot formed in a handle of the cordless drill. This allows the arrangement of a readout device or at least an antenna of the readout device at a distal end/end portion of the accumulator in such a way that with its complete insertion into the receptacle shaft, the readout device/antenna comes to rest close to the RFID tag and thus allows interference-free transmission of data.

Figure 21:
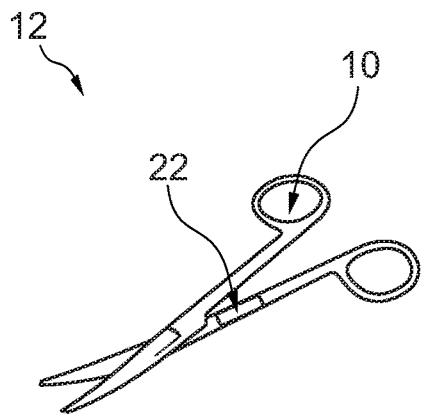
FIG. 21 is a representation illustrating an example of a medical instrument with an RFID tag holder.

FIG. 21 is a representation illustrating an example of a medical instrument 12 in the form of a pair of scissors, the two handle branches of which are suitable as instrument body 10 for receiving an RFID tag in an underfloor manner. In this preferred example, the holder 22 is formed in the form of a receiving pocket in one of the two handle branches, in particular in the branch region between a scissor hinge and a finger eye. In connection with suitable storage systems comparable to the holder according to FIG. 18, defined positions of the scissors (e.g. half-open) can be specified, whereby the readout device is inevitably arranged below the RFID tag when the scissors are inserted into the holder.

Figure 22:
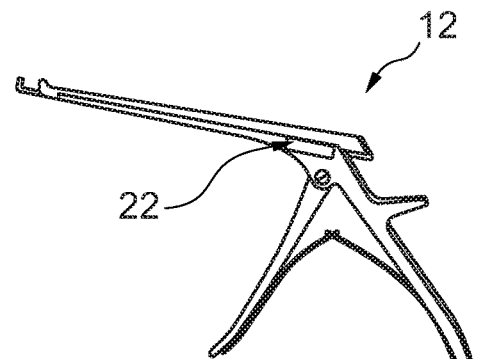
FIG. 22 is a representation illustrating an example of a medical instrument with an RFID tag holder.
Figure 23:
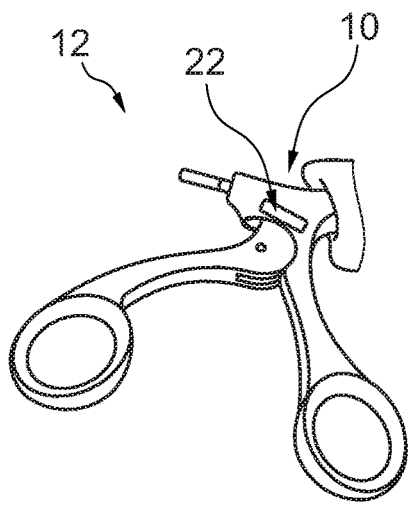
FIG. 23 is a representation illustrating an example of a medical instrument with an RFID tag holder.

FIGS. 22 and 23 each show a representation of another medical instrument 12 in the form of a punch consisting of a forceps handle and a punch carriage, which is guided longitudinally in a carriage shaft and is actuated via the forceps handle. In this example, the RFID tag holder 22 is preferably in the form of a receptacle adapter inserted into an instrument slit, wherein the instrument slit is located in the carriage shaft. This is particularly suitable in that it has sufficient wall thickness for the 'underfloor' receptacle of the RFID tag and also does not change its position when the forceps handle is moved. Therefore, this instrument 12 can be inserted into an instrument holder equipped with a readout device as shown in FIG. 18 without having to consider the current actuation state of the forceps handle, wherein the RFID tag is always located above the readout device.

Figure 24:
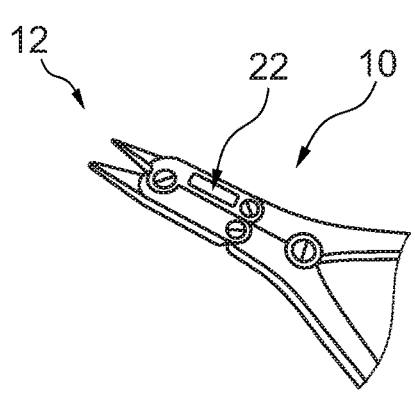
FIG. 24 is a representation illustrating an example of a medical instrument with an RFID tag holder.

FIG. 24 is a representation illustrating an example of a medical instrument 12 with RFID tag holder 22 in the instrument body 10, wherein said medical instrument is angle pliers. In the case of the angle pliers, the RFID tag is inserted into the surface of one of the two branches of the pliers in an 'underfloor' manner in the area of the engagement portions of the pliers and can be read out by suitable reading devices, which are comparable to the instrument holder as described in FIG. 18 above.

Figure 25:
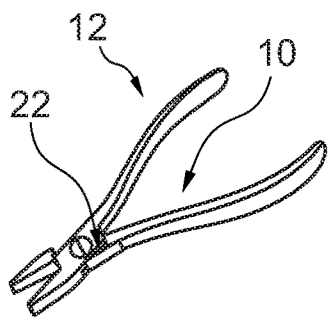
FIG. 25 is a representation illustrating an example of a medical instrument with an RFID tag holder.

FIG. 25 is a representation illustrating an example of a medical instrument 12 with RFID tag holder 22 in the instrument body 10, wherein said medical instrument is cutting or grasping forceps. In the illustrated cutting or grasping forceps, the RFID tag is embedded in the surface of a forceps branch and in particular in the handle portion of said forceps branch in an 'underfloor' manner and can be read out by suitable readout devices. In connection with storage systems or, respectively, holding systems in the sense of FIG. 18, defined actuation positions of the forceps may also be specified in this case, which allow the RFID tag to be arranged directly above the reading device.

Figure 26:
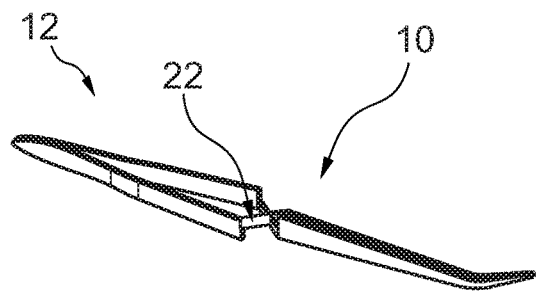
FIG. 26 is a representation illustrating an example of a medical instrument with an RFID tag holder.

FIG. 26 is a representation illustrating an example of a medical instrument 12 with RFID tag holder 22 in the instrument body 10, wherein said medical instrument is a pair of tweezers. In the tweezers, the RFID tag is inserted into the surface of a branch of the tweezers in particular in a branch center portion between the proximal tweezer handle and the distal engagement portion of the branch of the tweezers in an 'underfloor' manner and can be read out by suitable readout devices in the sense of FIG. 18.

FIGS. 27 to 31 show in a partial perspective view a medical instrument 12 according to the invention according to a further preferred embodiment as well as a method according to the invention for mounting a medical instrument according to a preferred embodiment, wherein in FIGS. 27 to 31 a successive, step-by-step assembly is illustrated. First the medical instrument 12 and then the method for assembly are described below.

Figure 27:
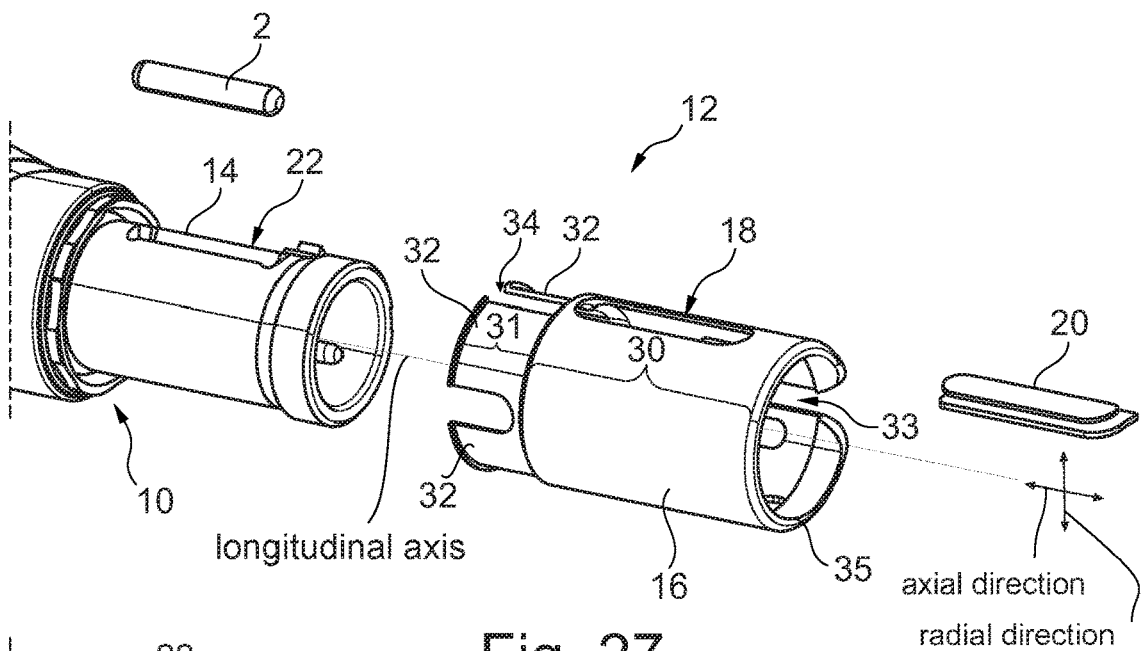

Specifically, the medical instrument 12 comprises the instrument body 10, the RFID tag 2 in the form of a pill-shaped glass tag, the separate metal shield 16 in the form of a clipable or, respectively, form-fittingly latchable metallic bushing and the signal-permeable cover 20 with rubber, silicone and/or plastic as material, wherein FIG. 27 shows in exploded view an unassembled state in which the above components are present separately. The instrument body 10 has a terminal, proximal, substantially cylindrical coupling portion with a longitudinal axis, in the radially outer circumferential wall of which an underfloor tag holder 22 in the form of a slit-shaped groove or, respectively, a recess is provided as a receiving pocket 14. In this embodiment, the radially outer part of the coupling portion of the instrument body 10 is made of plastic and thus signal-permeable. The groove-shaped receiving pocket 14 is adapted to (at least partially) receive the pill-shaped RFID tag 2 or, respectively, the RFID tag 2 can be inserted into the receiving pocket 14.

The metal shield 16 is divided in its axial direction into a proximal shielding portion 30 and a distal latching portion 31. The sleeve-shaped shielding portion 30 has the elongated and axially extending signal-permeable aperture opening 18 in the form of an elongated hole and, due to its metallic material, is used for signal shielding with a defined signal-permeable aperture opening 18 to increase a possible distance to a reading and/or writing device (not shown) as well as data transmission quality. The latching portion 31, on the other hand, is used to fix the metal shield 16 to the instrument body 10 in the axial direction, and on the other hand to define the relative positioning in the circumferential direction.

In particular, the shielding portion 30 is bushing-shaped/sleeve-shaped with a closed shell, in which defined openings or recesses are introduced only at individual points. These are mainly the aperture opening 18 and an incision 33 extending axially in the distal direction from the proximal end. This incision 33, which is rotated by 90° about the longitudinal axis relative to the aperture opening 18, can be used, for example, to define a relative positioning in the circumferential direction if, for example, a coupling portion complementary to the coupling portion with a defined projection extending radially inwards is introduced into the incision 33 in order to geometrically predetermine a relative rotational position of handpiece to counterpart.

Figure 31:
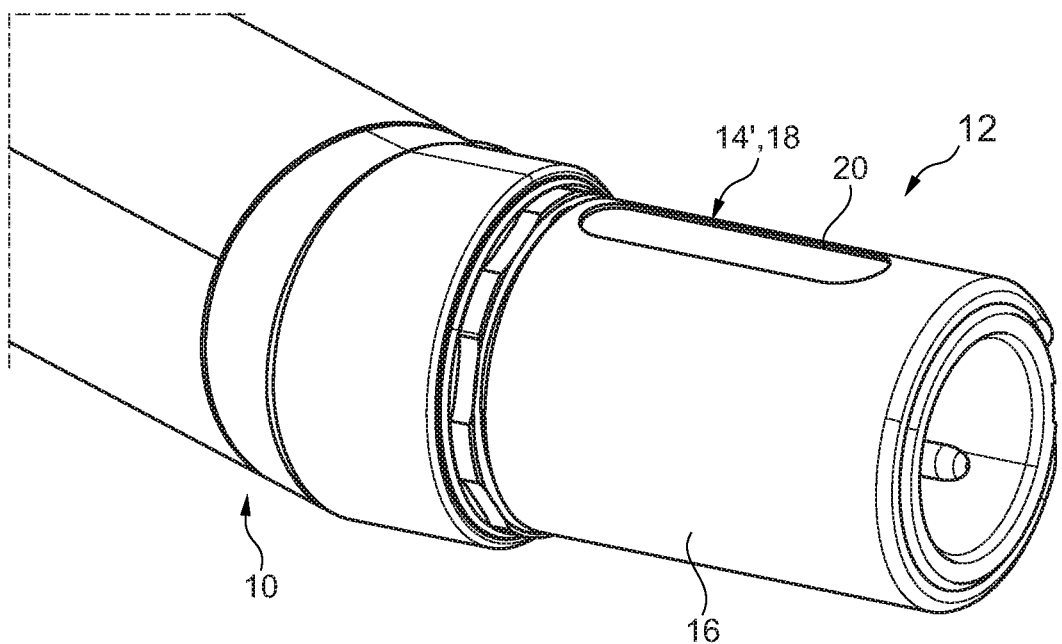

The latching portion 31, which directly adjoins the shielding portion 30 distally, has four part-circular latching arms 32 extending in the axial direction, which are in particular equally distributed when viewed in the circumferential direction. Each latching arm 32 has a detent projecting radially outwards at its distal end for form-fit engagement via an undercut. In extension of the aperture opening 18, a longitudinal recess 34 is provided between two such latching arms 32, so that the metal shield 16 can only be pushed onto the instrument body 10 in this position, which is fixed in the circumferential direction, when the RFID tag 2 is inserted. The metal shield 16 is thus adapted to be slid on and fixed in only one predetermined rotational position. As shown in FIG. 31, the RFID tag 2 and the aperture opening 18 are parallel and in radial extension to each other. This ensures that the aperture opening 18 is positioned symmetrically and centrally to the RFID tag 2, wherein the aperture opening 18 forms the opening 14' towards the surroundings of the instrument 12. Due to their geometric design, the latching arms 32 have a certain inherent elasticity in the radial direction in order to be temporarily deflected against their inherent tension. Preferably, only the shielding portion 30 may be made of metal and the latching portion 31 of another material, for example plastic.

The cover 20 made of rubber has a circumferential step in the radial direction or, respectively, two plate-shaped rectangles sitting one on top of the other with rounded corners with a dimension which decreases outwards in the radial direction, wherein the radially outer rectangle thereof has exactly the same dimension as the aperture opening 18 in order to close off the aperture opening 18 in a precise fit. The larger radially inner rectangle abuts the inner wall of the shielding portion 30. This design allows the cover 20 to be inserted into the inside of the metal shield 16 in the aperture opening 18 and to be held in place in the aperture opening 18 by only the RFID tag 2 as a counter element in the assembled state. The metal shield 16 has rounded edges 34 at its proximal end to facilitate insertion into a counterpart of the handpiece.

Figure 28:
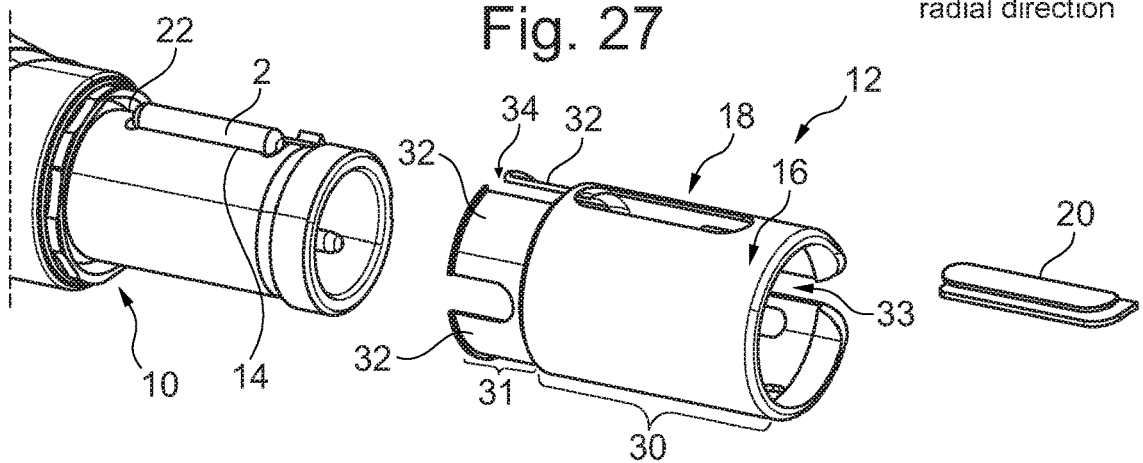
Figure 29:
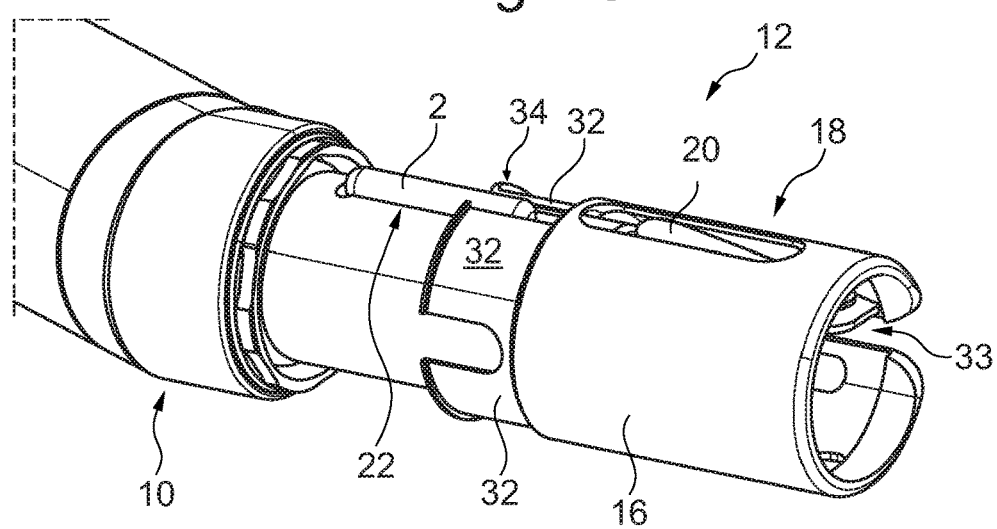
Figure 30:
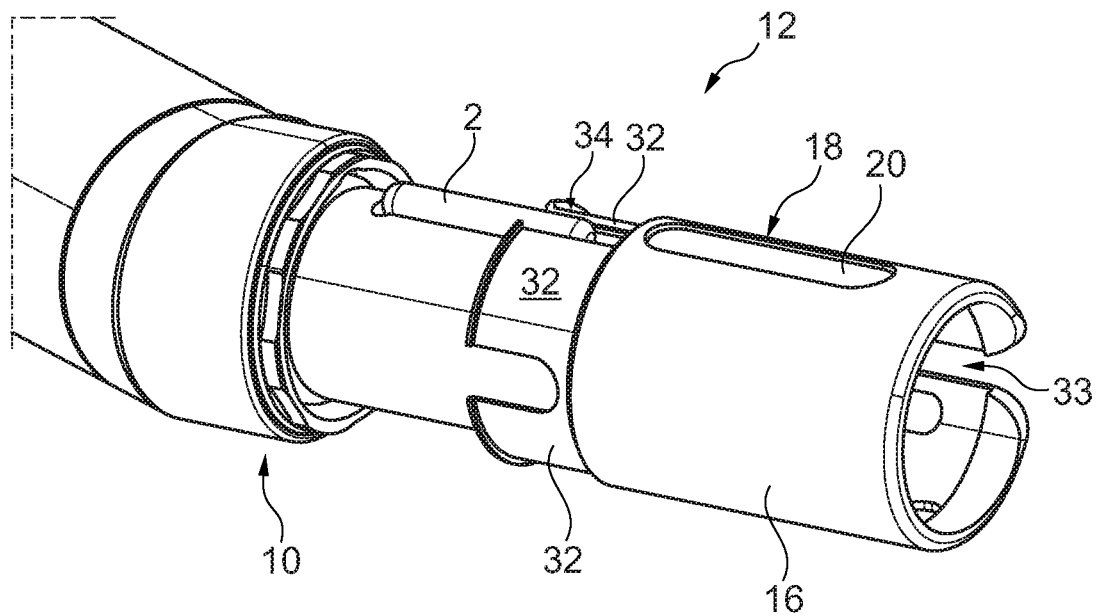

The method of assembly according to the invention is described below. In FIG. 27, a first step of positioning the RFID tag 2, the medical instrument 12, the metal shield 16 and the signal-permeable cover 20 relative to each other is shown. The metal shield is arranged coaxially with a longitudinal axis of the instrument body. In FIG. 28, a step of placing the RFID tag 2 into the underfloor tag holder 22 of the medical instrument 12 in the radial direction, in this case a press-fit in the radial direction into the underfloor tag holder 22, is shown. Of course, the step of placing the RFID tag 2 may also be performed first, followed by the step of positioning. Since the metal shield 16 is already in the correct rotational position relative to the instrument body 10, a step of rotating the metal shield 16 about an axial axis/longitudinal axis of the medical instrument 12 or respectively instrument body 10 until the signal-permeable aperture opening 18 and the RFID tag 2 are in the same position in the circumferential direction can be omitted. FIG. 29 shows partial placing of the cover 20 in the signal-permeable aperture opening 18 by moving the cover 20 in the axial direction into the metal shield 16 radially inwards and moving the cover 20 in the radial direction outwards into the aperture opening 16. The cover 20 is not completely inserted in the aperture opening 18. In addition, FIG. 29 shows partial sliding of the metal shield 16 onto the handpiece or respectively the medical instrument 12 with the inserted RFID tag 2 in the axial direction. Finally, FIG. 30 shows the completed step of inserting the cover 20 into the aperture opening 18, which closes flushly.

FIG. 31 shows the assembled state with the completed step of sliding the metal shield 16 onto the instrument body 10, so that the aperture opening 18 and the RFID tag 2 are arranged parallel and in radial extension to each other, and the RFID tag 2 is thus fixed in position in the medical instrument 12 in such a way that it cannot be lost. Also, the step of fixing the metal shield 16 with respect to the instrument body 10 was performed by latching the detents 32.

Finally, it should be noted that the terms 'holder' and 'tag carrier' are synonymous and stand for the same components. Furthermore, the exemplarily illustrated medical instruments are not restrictive, but any other instruments and possibly even orthoses or implants can be equipped with RFID tags placed in an 'underfloor' manner, such as cardiac pacemakers, artificial joints, etc. In summary, the invention relates to a medical instrument 12 having an instrument body 10 provided with an RFID tag 2. According to the invention, an RFID tag holder 22 is provided or formed in the instrument body 10, which is intended and formed/adapted to receive the RFID tag 2 in a position-fixing manner, such that the RFID tag 2 is exposed to the surroundings of the instrument 12 via an opening 14' formed in an instrument body surface, but is set back with respect to this instrument body surface in the direction of the instrument body interior, in order to preferably avoid protruding (of the RFID tag 2) beyond the instrument body surface.

The invention claimed is:

1. A medical instrument with an instrument body provided with an RFID tag, the medical instrument comprising an underfloor tag holder which is provided and formed to receive the RFID tag in a position-fixing manner such that the RFID tag is exposed to the surroundings of the instrument via an opening formed in an instrument body surface, but is set back with respect to this instrument body surface in the direction of the instrument body interior, in order to avoid protruding beyond the instrument body surface, wherein the underfloor tag holder with the RFID tag is surrounded, at least in sections, by a metal shield that is separate, the metal shield comprising an aperture opening that is signal-permeable, wherein the aperture opening is aligned with the opening, and wherein the opening is not closed by an RF shielding cover when the medical instrument is in a fully assembled state.

2. The medical instrument according to claim 1, wherein the instrument body encloses or has a hollow space which has access via the opening to an area surrounding the medical instrument, and wherein the underfloor tag holder comprises a tag carrier that is cartridge-like or cylindrical, the underfloor tag holder being inserted into the hollow space.

3. The medical instrument according to claim 2, wherein the tag carrier has a receiving pocket for the RFID tag, which is formed on an outer side of the tag carrier and comprises a pocket opening towards the outer side of the tag carrier, and wherein the receiving pocket is placed on the tag carrier in such a way that the pocket opening overlaps with the opening formed in the instrument body surface when the tag carrier is inserted into the hollow space.

4. The medical instrument according to claim 3, wherein the opening' formed in the instrument body surface is larger than the pocket opening, and wherein the pocket opening is smaller than the RFID tag inserted in the receiving pocket.

5. The medical instrument according to claim 4, wherein the opening formed in the instrument body surface has a width equal to $D_C*A$, wherein:
   $D_C$ is a coil diameter of the RFID tag; and
   A is between 1.3 and 2.2.

6. The medical device according to claim 4, wherein the opening in the instrument body surface has a length equal to $L_C*B$, wherein:
   $L_C$ is a total length of a ferrite core of the RFID tag or of the RFID tag; and
   B is between 0.7 and 1.5.

7. The medical instrument according to claim 1, wherein the instrument body is formed with a receiving pocket open to an outside of the instrument body for positionally fixed direct or indirect reception of the RFID tag.

8. The medical instrument according to claim 7, further comprising a receptacle adapter inserted into the receiving pocket and forming the underfloor tag holder.

9. The medical instrument according to claim 3, further comprising a cover or a cover-forming filling material made of a signal-permeable material, the cover or the cover-forming filling material being inserted or filled in the receiving pocket in such a way that the cover or the cover-forming filling material covers the RFID tag and creates a flush transition with the instrument body surface.

10. The medical instrument according to claim 1, wherein the underfloor tag holder comprises metal or a signal-permeable material.

11. The medical instrument according to claim 1, wherein the metal shield is formed as a sleeve or bushing with a circumferential lateral surface, the aperture opening being formed in the circumferential lateral surface.

12. The medical instrument according to claim 1, wherein the metal shield comprises an elongated washer or an annular metal sheet.

13. The medical instrument according to claim 1, wherein the aperture opening is elongated or slot-shaped and has a longitudinal axis, wherein a longitudinal axis of the RFID tag is arranged parallel to the longitudinal axis of the aperture opening and is spaced therefrom.

14. A medical treatment system comprising:
   the medical instrument according to claim 1; and
   a reading and/or writing device configured to be signal-technically coupled to the RFID tag, the reading and/or writing device comprising an instrument holder adapted for holding or temporarily fixing the medical instrument in a predetermined position and/or orienting relative to the reading and/or writing device, where a signal transmission between the RFID tag and the reading and/or writing device is enabled.

15. A method for assembling the medical instrument according to claim 1, the method comprising the steps of:
   A) positioning the RFID tag, the medical instrument and the metal shield relative to each other;
   B) placing the RFID tag into the underfloor tag holder by placing the RFID tag in a radial direction; and
   C) sliding the metal shield onto the medical instrument in an axial direction, so that the aperture opening and the RFID tag are arranged in radial extension to each other as seen in a longitudinal axis direction and thereby the RFID tag is fixed in position in the medical instrument so that the RFID tag cannot be lost.

16. The method according to claim 15, further comprising the following steps prior to step C):
   positioning a cover relative to the metal shield, the cover being signal-permeable; and
   placing the cover in the aperture opening by sliding the cover radially inwards in the axial direction into the metal shield and sliding the cover outwards in the radial direction into the aperture opening, so that the cover is inserted into the aperture opening,
   wherein, after step C), the cover is fixed in position in the medical instrument so that the cover cannot be lost.

17. The method according to claim 15, further comprising the following steps:
   after step A), rotating the metal shield around an axial axis of the medical instrument until the aperture opening and the RFID tag are in a same position in a circumferential direction; and
   after step C), fixing the metal shield.

18. A medical instrument comprising:
   instrument body surface defining an opening that exposes an interior space of the medical instrument to an exterior area of the medical instrument;
   a tag holder recessed in the instrument body surface, the tag holder comprising a metal shield having an aperture opening; and
   an RFID tag that is receivable in the tag holder in a position-fixing manner,
   the aperture opening of the tag holder being aligned with the opening in the instrument body surface, and
   the opening being signal permeable to allow data transmission to occur when the RFID tag is received in the tag holder.

19. The medical instrument according to claim 18, wherein the opening in the instrument body surface is closed by a signal permeable cover.

20. The medical instrument according to claim 18, wherein the opening in the instrument body surface is not closed by a cover.

* * * * *